United States Patent [19]
Wuest et al.

[11] Patent Number: 5,312,974
[45] Date of Patent: May 17, 1994

[54] PROCESS FOR THE PRODUCTION OF LIGHT-COLORED LOWER ALKANE-SULFONIC ACIDS, MORE PARTICULARLY METHANESULFONIC ACID

[75] Inventors: Willi Wuest, Ratingen; Rainer Eskuchen, Duesseldorf; Christoph Lohr, Dortmund, all of Fed. Rep. of Germany

[73] Assignee: Henkel Kommanditgesellschaft auf Aktien, Duesseldorf, Fed. Rep. of Germany

[21] Appl. No.: 778,825
[22] PCT Filed: Jun. 19, 1990
[86] PCT No.: PCT/EP90/00962
§ 371 Date: Dec. 19, 1991
§ 102(e) Date: Dec. 19, 1991
[87] PCT Pub. No.: WO91/00268
PCT Pub. Date: Jan. 10, 1991

[30] Foreign Application Priority Data

Jun. 28, 1989 [DE] Fed. Rep. of Germany ....... 3921131

[51] Int. Cl.$^5$ .............................................. C07C 61/00
[52] U.S. Cl. ..................................... 562/120; 562/124
[58] Field of Search ........................ 562/120, 124, 123

[56] References Cited

U.S. PATENT DOCUMENTS 3,453,320  7/1969  Robeson et al. ..................... 562/120

FOREIGN PATENT DOCUMENTS 3812846  11/1989  Fed. Rep. of Germany ...... 562/120

Primary Examiner—José G. Dees
Assistant Examiner—Keith MacMillan
Attorney, Agent, or Firm—Ernest G. Szoke; Wayne C. Jaeschke; John E. Drach

[57] ABSTRACT

The description is of a process for the production of light-colored lower alkane sulfonic acids, especially methane sulphonic acid, by reacting the corresponding alkyl halide with alkaline halides and obtaining the free alkane sulphonic acid. In the process of the invention, the reaction is performed as a liquid/liquid reaction at temperature not exceeding 120 degrees C., and at such high pressures that even the lower alkyl halide is in the liquid phase at the reaction temperature, the aqueous reaction mixture is reduced by water content of some 50% wt. at the most, the alkaline sulphonic acid is liberated from its alkaline salt by the addition of HCl, the solid salt phase still remaining in the reaction mixture is separated out and the free alkaline sulphonic acid is obtained from the liquid phase. To obtain an alkane sulphonic acid which is virtually free of chloride ions, the primary reaction product concentrated into the aqueous salt sludge by the partial removal of water is preferably converted with a multi-molar excess of HCl is extracted from the isolated liquid phase and virtually chloride-free alkane sulphonic acid is obtained together with the residual water as the basic phase of distillation.

17 Claims, No Drawings ic-COLORED LOWER ALKANE-SULFONIC
ACIDS, MORE PARTICULARLY
METHANESULFONIC ACID

PROCESS FOR THE PRODUCTION OF LIGHT-COLORED LOWER ALKANE-SULFONIC ACIDS, MORE PARTICULARLY METHANESULFONIC ACID

BACKGROUND OF THE INVENTION

1. Field of the Invention

This invention relates to an improved process for the production of light-colored lower alkanesulfonic acids by reaction of the corresponding alkyl halides with alkali metal sulfite in aqueous solution at elevated temperature and pressure and subsequent separation of the alkali metal halide, release of the alkanesulfonic acid formed and recovery thereof.

2. Statement of Related Art

More particularly, the invention seeks to provide high-purity alkanesulfonic acids which are suitable for use, for example, in the field of industrial detergents. This requires above all the maintenance of low maximum levels of chloride ion contamination in the alkanesulfonic acid. At present, industrial quantities of high-purity alkanesulfonic acids are not available at acceptable prices. Accordingly, the object of the invention is to provide access to the particularly interesting class of $C_{1-6}$ alkanesulfonic acids, preferably the corresponding free sulfonic acids containing 1 to 4 carbon atoms, which are suitable for use in practice precisely because of their reasonable price. Methanesulfonic acid is particularly important in this regard. The starting materials required for its production are available in large quantities as inexpensive chemicals.

Short-chain alkanesulfonic acids can be produced by oxidation of the corresponding mercaptans with nitric acid or peracids and with iodine in the presence of bromide ions in dimethyl sulfoxide. Unfortunately, these processes only give moderate yields. In addition, mercaptans are too expensive for industrial processes.

In addition, short-chain alkanesulfonic acids can be produced from alkanes by sulfochlorination and subsequent saponification of the alkanesulfonyl chloride or by sulfoxidation. However, the sulfonation reaction takes place at the hydrocarbon chain in statistical distribution and, in addition, may even take place several times, so that 1-sulfonic acids cannot be selectively produced.

The reaction of olefins with sodium hydrogen sulfite and subsequent release of the alkanesulfonic acids also gives unwanted secondary products.

The reaction of short-chain alkyl halides with sodium sulfite to form the corresponding alkyl sodium sulfonates by the so-called Strecker synthesis is known from Bl. Chem. Soc. Japan 32, 850 (1959). However, the release of the short-chain alkanesulfonic acids from the sodium salts obtained is not described. In fact, it also involves difficulties because both the short-chain alkanesulfonic acids and their salts and also the sodium salts formed as secondary reaction products are highly soluble in water. Accordingly, the desired alkanesulfonic acid cannot simply be extracted from the reaction mixture formed.

Applicants' earlier patent application DE 3812846 A1 "A process for the production of $C_{1-6}$ alkanesulfonic acids" relates to a process for the production of linear or branched $C_{1-6}$ alkanesulfonic acids from their alkali metal salts which is characterized in that the alkali metal salts are reacted with hydrogen chloride in a solution or suspension in $C_{1-4}$ monoalkanols, the alkali metal chlorides precipitated are separated and the $C_{1-6}$ alkanesulfonic acids are isolated from the monoalkanol phase. The Examples of this earlier application describe the production of the particular sodium salts of the alkanesulfonic acids in question by the Strecker synthesis by reaction of the corresponding alkyl chlorides with sodium sulfite in aqueous solution at 150° C. over a reaction time of 8 hours. The corresponding sodium salt of methanesulfonic acid is prepared by a 12-hour reaction in an autoclave at 100° C. Comparatively limited final reaction pressures are established.

By contrast, the problem addressed by the present invention was firstly to establish reaction conditions under which the alkali metal salts and particularly the sodium salts of the lower alkanesulfonic acids in question, particularly methanesulfonic acid, could be produced considerably more economically and, secondly, to provide a simple method of separating the free alkanesulfonic acid from the aqueous solutions of the sodium salts formed, preferably without having to use auxiliary solvents in the form of the lower monoalkanols from the teaching of the earlier application cited above.

SUMMARY OF THE INVENTION

In a first embodiment, therefore, the present invention relates to a process for the production of light-colored lower alkanesulfonic acids, more particularly methanesulfonic acid, by reaction of the corresponding alkyl halides in aqueous solution with alkali metal disulfite at elevated temperature and pressure and subsequent separation of the alkali metal halide and recovery of the free alkanesulfonic acid. The new process is characterized in that the reaction is carried out as a liquid/liquid reaction at temperatures of at most about 120° C. and under such high pressures that even the lower alkyl halide used is present in liquid form at the reaction temperature, in that the aqueous reaction mixture formed is worked up by partial removal of water to form an aqueous suspension containing crystallized salt phases and having a residual water content of at most about 50% by weight, the alkanesulfonic acid is then released from its alkali metal salt by addition of hydrogen chloride, the solid salt phase now present in the reaction mixture is separated and the free alkanesulfonic acid is recovered from the liquid phase.

DESCRIPTION OF THE PREFERRED EMBODIMENTS

The teaching according to the invention is illustrated in the following with reference to the production of methanesulfonic acid using methyl halide, more particularly methyl chloride. However, it may also be similarly applied to the production of other lower alkanesulfonic acids of the described type, more particularly those containing up to 6 and preferably up to 4 carbon atoms.

The reaction of the methyl chloride with the reaction component yielding sulfite ions takes place in aqueous solution under such temperature and pressure conditions that the reaction takes place as a liquid/liquid reaction. Reaction temperatures below 100° C. and preferably of at most 90° C. are used to suppress the formation of unwanted secondary products. Maximum reaction temperatures of up to about 80° C. are particularly suitable. Since, on the other hand, the reaction rate falls drastically at temperatures below 70° C., temperatures in the range from about 70° to 80° C. have proved to be particularly suitable.

The reaction pressures applied are above 10 bar and are preferably at least 15 bar. Pressures in the range from 15 to 30 bar are particularly suitable, pressures of 18 to 20 bar being particularly appropriate for the production of methanesulfonic acid.

Under these operating conditions, the liquid/liquid reaction may be carried out, for example, in a pressure reactor in the form of a stirred tank reactor. It has been found that the comparatively high reaction pressures accelerate the reaction to a considerable extent, so that under pressures in the range mentioned the reaction can be carried out in reaction times of at most about 1 hour and preferably in reaction times of up to about half an hour, the desired conversion levels still being achieved. In one preferred embodiment for the production of methanesulfonic acid, reaction times of about 2 to 20 minutes under the preferred temperature and pressure conditions mentioned are sufficient to achieve the required conversion.

Sodium sulfite in the form of an aqueous solution may be used as the sulfite-yielding reactant. However, one preferred embodiment of the invention is characterized by the use of the less expensive alkali metal disulfite, i.e. in particular sodium disulfite $Na_2S_2O_5$, which—together with stoichiometric quantities of alkali metal hydroxide, particularly sodium hydroxide—leads to the intermediate formation of sodium sulfite. In this embodiment, the total starting material costs can again be substantially reduced. The reaction of the sodium disulfite with sodium hydroxide in aqueous solution is best carried out before the methyl chloride is introduced into the aqueous reaction phase.

On completion of the reaction between the alkyl halide, more particularly the methyl chloride, and the aqueous sodium sulfite solution, the reaction mixture formed is worked up. Working up may be carried out in accordance with the teaching of the earlier patent application DE 3812846 A1 cited above. In one particularly important embodiment of the invention, however, elements of the process described in parallel patent application PCT/ED 90/00943 "A process for the production of lower alkanesulfonic acids from their alkali metal salts") are incorporated in this working-up stage. In this embodiment, the teaching of the invention combines the process features of both patent applications. In order to complete the disclosure of the invention, the key measures involved in this subsequent working-up stage are reiterated in the following:

In this preferred embodiment, an alkanesulfonic acid substantially free from chloride ions is obtained by addition of a multiple molar excess of hydrogen chloride, based on alkanesulfonic acid, to the alkali metal salts of the alkanesulfonic acid, if desired in admixture with alkali metal chloride, in the form of a concentrated aqueous salt suspension, the solid phase then present is separated, the excess hydrogen chloride is removed from the isolated liquid phase by distillation, if desired together with part of the water, and the substantially chloride-free alkanesulfonic acid is recovered together with the residual water as the bottom phase of the distillation process. The reaction product initially obtained is preferably concentrated before addition of the HCl to such a extent that the salt suspension still just flows and can be pumped.

The crux of the teaching according to the invention is the surprising observation that, by using a considerable excess of HCl in the conversion of the alkali metal salt of the alkanesulfonic acids present in aqueous solution or suspension with release of the free acid and simultaneous formation of the alkali metal chloride, the solubility of the alkali metal chloride in the concentrated aqueous phase can be reduced to such an extent that the alkali metal can be removed substantially quantitatively by simple phase separation. The free alkanesulfonic acid is present together with the HCl excess used in the aqueous liquid phase obtainable in this way. As will be described hereinafter, the hydrogen chloride can be separated under moderate conditions, any residues of hydrogen chloride being removable by distillation in the form of an aqueous azeotrope, so that a light-colored, free alkanesulfonic acid substantially free from chloride ions and containing variable quantities of water can ultimately be obtained.

This embodiment of the working-up stage is particularly suitable for the production of $C_{1-4}$ alkanesulfonic acids. Methanesulfonic acid in particular can easily be recovered from its alkali metal salts by the new process. The preferred alkali metal salts for the described reaction according to the invention are the sodium salts.

The crucial process aid which enables the type of reaction described herein to be carried out in aqueous medium is the use of the hydrogen chloride in excess in the release of the alkanesulfonic acid, more particularly in a multiple molar excess. Hydrogen chloride is preferably used in at least about 3 times the molar quantity, based on alkanesulfonic acid alkali metal salt present. This HCl excess is not problematical to the overall balance of the process because those parts of the hydrogen chloride which are not required for salt formation can be recycled to the next process stage. The HCl is normally used in quantities of at most about 5 mol, based on the alkali metal salt of the alkanesulfonic acid. Quantities of from about 3.2 to 4 mol HCl have proved to be particularly suitable.

After the treatment of the alkali salt of the alkanesulfonic acid—used in the form of an aqueous salt suspension—with the hydrogen chloride, which may be used in free form and/or as an aqueous solution, for example as fuming hydrochloric acid, a suspension of alkali metal chloride, particularly sodium chloride, in a liquid phase containing the free alkanesulfonic acid together with HCl in dissolved form is formed. The solubility of the sodium chloride in this liquid is negligible through the excess of HCl. The sodium chloride present in solid form is suitably separated from the liquid phase, for example by filtration or centrifugation. This separation may be carried out at normal temperature or, at best, moderately elevated temperatures, i.e. for example at temperatures of up to about 60° C. In many cases, suspensions in the temperature range from about 40° to 60° C. are present at the time when phase separation is carried out, being suitable for the separation stage by virtue of these temperatures.

Subsequent separation of the liquid phase obtained may be carried out by distillation, more particularly in multiple-stage form. In the most simple form, separation is carried out by a two-stage distillation process in which the hydrogen chloride is first driven off and returned to the main process. In the final stage of this separation of the liquid phase, an HCl/water mixture can be separated, preferably in a light vacuum, so that temperatures below 100° C. can be maintained, temperatures of the liquid phase in the range from about 80° to 90° C. being particularly suitable. The HCl/water azeotrope separated in the second stage of the process may also be recycled to the main reaction, so that only the circulated quantity of water need be taken into consideration.

After separation of the hydrogen chloride and limited quantities of water from the liquid phase, the free alkanesulfonic acid in the form of a light-colored, chloride-free reaction product accumulates as the bottom phase. In one preferred embodiment of the invention, the water balance of the process as a whole is controlled in such a way that the free alkanesulfonic acid accumulating in turn has a small residual water content of at least about 1 to at most about 30% by weight and preferably of about 10 to 20% by weight. To this end, the water content of the aqueous salt suspension used in the release of the alkanesulfonic acid merely has to be selected so that, despite removal of part of the aqueous phase with the remaining excess quantities of HCl during the complete removal of the HCl by distillation, the desired water content remains behind in admixture with the alkanesulfonic acid released.

The highly concentrated alkanesulfonic acids thus obtained may be put to their intended use, if desired after dilution with more water. The chloride content of the alkanesulfonic acids lies in the acceptable trace range. For example, it is readily possible by the described method to obtain methanesulfonic acid from its sodium salt with chloride contents well below 500 ppm.

The above-described separation of the excess hydrochloric acid by distillation, more particularly in the form of an aqueous azeotrope, may be carried out, for example, in falling-film evaporators which are constructed from such materials that they are not damaged by the basically aggressive medium. Materials and apparatus of this type are known from the prior art and include, for example, corresponding apparatus based on graphite.

EXAMPLES

Experimental Set-up

The tests were carried out in a 2.5 l autoclave ($P_{max}$ 30 bar) equipped with an anchor stirrer. The methyl chloride was introduced through a flanged-on gas cylinder. For heating and cooling, the double-jacketed autoclave was connected to a thermostat.

Test Procedure

A sodium hydrogen sulfite solution prepared from solid $Na_2S_2O_5$ and $H_2O$ was initially introduced into the reactor and then reacted with a stoichiometric quantity of 50% NaOH to form the sulfite solution. The methyl chloride was then introduced very rapidly into the reaction solution heated to 60° C. in the reactor from a gas cylinder. To enable the liquid gas to be rapidly introduced, the cylinder had previously been brought with nitrogen to an internal pressure of approximately 30 bar.

EXAMPLE 1

Primary Reaction 1,500 g of a 20% by weight hydrogen sulfite prepared from $N_2S_2O_5$ and $H_2O$ were initially introduced into the reactor and reacted with 230 g NaOH (50%) to form a 21% sodium sulfite solution. After heating to 60° C., 146 g methyl chloride were rapidly introduced into the reactor from a gas cylinder by the method described above. The reaction solution underwent an increase in temperature to 85° C., the pressure rising briefly to 24 bar. The reaction was terminated after about 90 seconds.

The composition of the solution in % by weight was as follows:
$CH_3SO_3^-$: 14.5%
$SO_3$: less than 0.1%
$Cl^-$: 5.4%
Methanol: less than 200 ppm
Dimethyl ether: less than 50 ppm.

EXAMPLE 2

Primary Reaction 1 500 g of a 28.5% by weight hydrogen sulfite prepared from $Na_2S_2O_5$ and $H_2O$ were initially introduced into the reactor and reacted with 360 g NaOH (50) to form a 30.5% sodium sulfite suspension. After heating to 60° C., 230 g methyl chloride were rapidly introduced from a gas cylinder by the method described above. The reaction solution initially underwent a rapid increase in temperature to 80° C. A temperature of 75° C. had to be maintained for 20 minutes by means of the thermostat to complete the reaction of the educts. After the end of the reaction, the now clear salt solution had the following composition:
$CH_3SO_3^-$: 20%
$SO_3$: less than 0.1%
$Cl^-$: 7.6%
Methanol: less than 200 ppm
Dimethyl ether: less than 50 ppm.

WORKING UP TO THE FREE ACID

In a rotary evaporator, 1,000 g of the solutions prepared in accordance with Examples 1 and 2 were concentrated in a water jet vacuum to a minimal residual moisture content (less than 5%). 300 g of the salt thus obtained were taken up in 450 g fuming hydrochloric acid (37%). After the NaCl precipitated had been filtered off, the hydrochloric acid/methanesulfonic acid mixture was concentrated in a water jet vacuum at 110° C. in a rotary evaporator to a concentration of 80% by weight methylenesulfonic acid and 20% water. The chloride concentration was less than 200 ppm $Cl^-$ and the yield amounted to 98%, based on the sulfonate salt used.

What is claimed is:

1. A process for producing a light-colored, lower alkane sulfonic acid comprising the steps of: (a) reacting an alkyl halide having up to six carbon atoms with an alkali metal sulfite in an aqueous medium at a temperature of up to about 120° C. and a pressure sufficient to keep said alkyl halide in the liquid phase to form an aqueous reaction mixture comprised of an alkali metal salt of said alkane sulfonic acid and an alkali metal halide; (b) removing a portion of the water from said aqueous reaction mixture to form an aqueous suspension containing crystallized salt phases, said lower alkane sulfonic acid, and up to about 50% by weight of water; (c) adding hydrogen chloride to said aqueous suspension to form solid alkali metal halide and a first aqueous solution comprising said alkanesulfonic acid and said hydrogen chloride wherein the molar ratio of hydrogen chloride to said alkane sulfonic acid is at least 3 to 1; (d) separating said solid alkali metal halide from said first aqueous solution to form a second aqueous solution comprised of said alkane sulfonic acid and hydrogen chloride.

2. The process of claim 1 wherein said alkyl halide is an alkyl chloride having from 1 to 4 carbon atoms.

3. The process of claim 2 wherein said alkyl halide is methyl chloride.

4. The process of claim 1 wherein in step (a) said alkali metal sulfite is formed by reaction of an alkali metal disulfite and a stoichiometric quantity of an alkali metal hydroxide.

5. The process of claim 4 where said alkali metal disulfite is $Na_2S_2O_5$ and said alkali metal hydroxide is sodium hydroxide.

6. The process of claim 1 wherein said pressure is at least 10 bar.

7. The process of claim 3 wherein said pressure is at least 15 bar and the temperature is less than about 100° C.

8. The process of claim 3 wherein the process is carried out at a pressure of from about 15 to about 30 bar and at a temperature in the range from about 70 to about 80° C. and over a time period of less than 60 minutes.

9. The process of claim 8 wherein said time period is in the range from about 2 to about 20 minutes.

10. The process of claim 1 wherein step (b) is carried out at a at temperature of less than about 100° C.

11. The process of claim 10 wherein step (b) is carried out at a reduced pressure.

12. The process of claim 1 wherein said molar ratio is from about 3.2 to 1 to about 4 to 1.

13. The process of claim 1 further comprising the step of removing said hydrogen chloride and a portion of the water from said second aqueous solution to form a mixture comprised of water and said alkane sulfonic acid.

14. The process of claim 12 wherein said hydrogen chloride is removed by a two-stage distillation operation wherein the first stage of said operation is the removal of hydrogen chloride and the second stage is the removal of a hydrogen chloride/water azeotrope.

15. The process of claim 14 wherein said distillation operation is carried out at temperature in the range from about 80 to about 90° C. and under reduced pressure.

16. The process of claim 1 wherein said alkane sulfonic acid in said mixture is comprised of at least about 1 to about 30% by weight water.

17. The process of claim 16 wherein the amount of said water is from about 10 to about 20% by weight.

* * * * *

UNITED STATES PATENT AND TRADEMARK OFFICE
CERTIFICATE OF CORRECTION

PATENT NO.   :   5,312,974
DATED        :   May 17, 1994
INVENTOR(S)  :   Willi Wuest et. al.

It is certified that error appears in the above-indentified patent and that said Letters Patent is hereby corrected as shown below:

In claim 14, column 8, line 11, "claim 12", should read:
              -- claim 13 --.

In claim 16, column 8, line 19, "claim 1", should read:
              -- claim 13 --.

Signed and Sealed this

Sixteenth Day of May, 1995

Attest:

BRUCE LEHMAN

*Attesting Officer*      *Commissioner of Patents and Trademarks*